(12) United States Patent
Meyer et al.

(10) Patent No.: US 9,707,118 B1
(45) Date of Patent: Jul. 18, 2017

(54) ROOSTER BOOT ANKLE FOOT ORTHOSIS

(71) Applicant: G.C. Meyer Inc., Muskegon, MI (US)

(72) Inventors: Grant C. Meyer, Muskegon, MI (US); Daniel R. Ware, Grand Rapids, MI (US)

(73) Assignee: Grant C. Meyer, Muskegon, MI (US)

( * ) Notice: Subject to any disclaimer, the term of this patent is extended or adjusted under 35 U.S.C. 154(b) by 454 days.

(21) Appl. No.: 13/668,594

(22) Filed: Nov. 5, 2012

Related U.S. Application Data (63) Continuation-in-part of application No. 12/658,427, filed on Feb. 5, 2010.

(51) Int. Cl.
*A61F 5/00* (2006.01)
*A61F 5/01* (2006.01)

(52) U.S. Cl.
CPC .................. *A61F 5/0127* (2013.01)

(58) Field of Classification Search
CPC .......... A61F 5/0111; A61F 5/0113; A61F 2005/0132; A61F 2005/0165; A61F 2005/0167; A61F 5/0585
USPC ................. 302/27, 28, 23, 16; 128/882
See application file for complete search history.

(56) References Cited

U.S. PATENT DOCUMENTS

| | | |
|---|---|---|
| 4,669,142 A | 6/1987 | Meyer |
| 4,756,096 A | 7/1988 | Meyer |
| 4,934,355 A | 6/1990 | Porcelli |
| 5,036,837 A | 8/1991 | Mitchell et al. |
| 5,044,360 A | 9/1991 | Janke |
| 5,358,469 A | 10/1994 | Patchel et al. |
| 5,429,588 A * | 7/1995 | Young .................. A61F 5/0127 36/28 |
| 5,486,157 A | 1/1996 | DiBenedetto |
| 5,542,912 A * | 8/1996 | Hess .................. A61F 5/0585 128/882 |
| 5,611,773 A * | 3/1997 | Nash .................. A43B 7/20 602/16 |

(Continued)

OTHER PUBLICATIONS

Print out of website www.dynasplint.com dated Feb. 1, 2010 and cited in co-pending U.S. Appl. No. 12/658,427, filed Feb. 5, 2010.

(Continued)

*Primary Examiner* — Victoria J Hicks
(74) *Attorney, Agent, or Firm* — Gardner, Linn, Burkhart & Flory, LLP (57) ABSTRACT

An ankle foot orthosis that may be used for children with lower extremity spasticity or muscle weakness to prevent deformity and enhance extremity function. The orthosis includes an adjustable tension assembly connected to an upper leg portion and a lower foot portion. The tension assembly includes a tension adjuster connected with an elastomer band, with the tension adjuster being operable to selectively increase or decrease the amount of stretch applied to the elastomer band to provide a selectable upward biasing force to a patient's foot. The dynamic orthosis creates a variable load stretch below the knee preventing muscle contracture, heel cord shortening, and increases range of motion and is utilized during rest, sleep, and short distant weight bearing providing readings of the range of motion continuously. The orthosis incorporates a circumferential dynamic support system that maintains corrected alignment of the bones of the foot and ankle.

28 Claims, 10 Drawing Sheets

(56) References Cited

U.S. PATENT DOCUMENTS

| | | |
|---|---|---|
| 5,749,840 A | 5/1998 | Mitchell et al. |
| D395,514 S | 6/1998 | Stano |
| 6,824,523 B2 * | 11/2004 | Carlson ................. A61F 5/0113 602/16 |
| 6,860,864 B2 | 3/2005 | Meyer |
| 7,101,346 B1 | 9/2006 | Davis |
| 7,182,743 B2 | 2/2007 | Slautterback et al. |
| 2005/0070834 A1 | 3/2005 | Herr et al. |

OTHER PUBLICATIONS

Specification and drawings from co-pending U.S. Appl. No. 12/658,427, filed Feb. 5, 2010.

* cited by examiner

ROOSTER BOOT ANKLE FOOT ORTHOSIS

CROSS REFERENCE TO RELATED APPLICATION

The present application is a continuation-in-part of U.S. nonprovisional patent application Ser. No. 12/658,427, filed Feb. 5, 2010, by Grant C. Meyer and Daniel R. Ware, which is hereby incorporated herein by reference.

BACKGROUND OF THE INVENTION

The present orthosis invention relates to an, ankle foot orthosis designed for increasing the range of motion and correcting the alignment of a patient's foot and ankle.

Children having spasticity, a condition often scene in cerebral palsy and similar types of medical disorders, are generally confronted with muscle imbalance, as their muscles do not work together in the manner of non-spastic children. The spasticity makes their muscles overpower other muscles creating unwanted pulls or forces on their joints. This imbalance of muscle pulls and involuntary forces, usually called spastic contractures, creates misalignment of involved joints. If this misalignment is not corrected and range of motion restored, it will eventually lead to permanent deformity as the child ages.

Plantar flexion is a normal position when the foot is flexed downward. A spastic contracture of the posterior tibial muscles (calf) can hold the foot in that position and produce a shortening of the heel cord called equinus. This type of positioning can also be seen when there is a weakening in the anterior muscles or dorsiflexors. This shortened heel cord can generate additional undesirable positions, which can lead to permanent deformity if not treated.

SUMMARY OF THE INVENTION

The present orthosis invention provides a lightweight boot for a patient to wear at night while asleep and/or at rest to increase the range of motion and correct the alignment of the foot and ankle complex. The orthosis is designed to provide adjustable dynamic stretch load to the posterior muscles and heel cord during sleep and rest to prevent contracture and shortening of the heel cord, including to lengthen and increase range of motion. The design of the orthosis provides total contact for pressure reduction, while maintaining corrected alignment. In a particular embodiment the orthosis comprises a posterior semi-rigid outer shell section joined with a foot shell section of the same material and a circumferential molded inner boot section, where the molded inner boot section retains the patient's corrected shape contours independent from the outer shell and foot shell.

The molded inner boot may be used in place of a pretibial shell and the tongue assembly may be reinforced with an additional layer of EVA or similar material under the dorsal strap over the foot's instep and the elastic Velcro strap attached to the tongue anterior to the tibia and fibula. The molded inner boot can be fabricated from thermal-formable foam in variable durometers, or in combination with other polymers (EVA co-polymers). The molded inner boot may be removed from the more rigid posterior outer shell if necessary for possible donning and other issues. The posterior section of the molded inner boot may be cut at the ankle axis to move in conjunction with the posterior and foot outer shells. The molded inner boot allows the natural rotation of the tibia of the ankle during dorsal and plantar flexion. The molded inner boot is fabricated from each individual patient's corrected casted mold, thereby promoting the holding and supporting of the corrected position. This corrected alignment resists the abnormal forces which are presented by the pathology that typically leads to deformity and/or progression of the anomaly. The present orthosis further comprises an adjustable tension or power pack assembly, including a power band and tension adjuster, and a variable position slotted locking plate assembly to provide stretch loads to the muscles and heel cord for achieving corrected alignment.

The orthosis promotes a low-load stretch during rest and sleep to improve the patient's range of motion. The orthosis foot section is pulled toward dorsiflexion by tension forces provided from the adjustable power pack assembly. The tension provided by the adjustable power pack assembly includes a tension adjuster segment, tension gauge with numerical indicia graduations, and a power band further including a slot and anchor pin located at the lower end. The tension adjuster further includes a threaded barrel insert at its upper end with a threaded bolt for insertion into the tension adjuster, and is also provided with an anchor pin at its upper end.

The adjustable locking assembly provides the ability to monitor and adjust the range of motion (ROM) in dorsi and plantar flexion, and also provides the patient care giver a numerical readout for indicating the patient's progress. The lightweight locking assembly can be provided with optional adjustments with a numerical monitoring (ROM) readout to a preferred dorsiflexion, plantar flexion, or other variable locked positions.

The orthosis has a sole and mid sole which provide a solid base of support for weight bearing and short distant ambulation. Upon weight bearing, the power pack assembly may be adjusted to relieve all tension at the ankle, allowing free motion at the ankle. The ROM can now be determined and monitored by the slotted locking plate assembly during various standing position. The forward flexion of the tibia and lower leg can be stopped at any desired position and adjusted with the locking assembly. During non-weight bearing and weight bearing, the molded inner boot is supported by the foot shell and posterior shell forces maintaining the desired corrected alignment.

Positioning the ankle with the adjustable locking assembly, while maintaining correct alignment throughout the foot during weight bearing use, is beneficial for optimum security and stability during walking with the present orthosis, such as for spastic patients or patients with weakened muscular ability. Locking or stopping the ankle motion at the various positions with the adjustable locking system will result in a change of ground reaction forces sent to the orthosis. These forces may be studied to provide optimum positioning for weight bearing, standing, and ambulation. A further optional design variation of the present orthosis may include an additional adjustable power pack on the opposite side.

The dynamic orthosis creates a variable load stretch at the ankle to prevent contracture of the heel cord and may be utilized during rest, sleep, and weight bearing use. The orthosis boot is light weight, non-cumbersome, and provides circumferential support and dynamic stabilizing forces while maintaining a corrected alignment of the bones of the foot and ankle. The orthosis boot provides range of motion improvements for dorsiflexion, thus preventing spastic contracture shortening of the heel cord, and includes monitoring and control features. The present orthosis boot is also utilized during weight bearing use and evaluation with the orthotic device providing the unique features in a simplified, lightweight, functional design.

DETAILED DESCRIPTION OF THE PREFERRED EMBODIMENTS

The present invention will now be described with reference to the accompanying figures, wherein the numbered elements in the following written description correspond to like-numbered elements in the figures. In the embodiment shown in FIGS. 1-4, the orthosis includes a molded inner boot or inner boot assembly 1, an upper or posterior shell 4, and a lower or foot shell 19, with shell 4 and shell 19 being rigidly formed of molded plastic and a sole 21 affixed to the bottom of foot shell 19. Also included are a static strap 3b and a stretchable elastic strap 3a used to secure a patient's foot and ankle within the orthosis, such as by hook and loop fastener connections to shell 19 and shell 4, respectively, in the illustrated embodiment. As shown in FIGS. 1-4 and 8, posterior shell 4 has a generally semi-cylindrical shape that conforms to the posterior lower calf and upper ankle region of a patient, with foot shell 19 including a wall portion 22 defining a heel receiving cavity and a base portion 23 that extends forward relative to wall portion 22 to provide toe support. As discussed in more detail below, the orthosis boot enables selective tensioning to be applied to a patient to stretch the patient's heel cord by applying an upward dorsiflexion force.

The orthosis includes an adjustable tension assembly or power pack assembly 5 connected to the posterior shell 4 and foot shell 19 forward of the joint 20. Assembly 5 includes an upper portion with a tension adjuster 6 having numerical readout gradations, a threaded receiving bore 7 and a threaded bolt 8 that is received in bore 7. Tension adjuster 6 includes an aperture or slotted window 6a through which the end of bolt 8 opposite its head 8a is visible to enable monitoring of the tension adjustment of assembly 5. Assembly 5 is connected to posterior shell 4 by way of a bracket 17 mounted to posterior shell 4 by fastener 9, where bracket 17 is generally L-shaped and includes a hole through which bolt 8 is passed with the head 8a of bolt 8 thereby supported on the bracket 17. Assembly 5 also includes a lower portion with an elastomer power band segment 18, where elastomer band 18 includes a slot 12 at one end for moveable connection to foot shell 19 at fastener or engagement pin 13, where pin 13 is also employed to secure strap 3b to shell 19. Band 18 is joined at its opposite end to tension adjuster 6 by way of another fastener 9a.

Posterior shell 4 is further connected with foot shell 19 by way of connecting joint 20, where joint 20 includes a flexible connector member 24 that is affixed within a cavity 25 of shell 4 by fastener 26a at one end, and is affixed within a cavity 27 of shell 19 by fastener 26b at its opposite end. A second joint 20a (FIG. 8) of substantially similar construction to joint 20 is located on the opposite side of the orthosis relative to a patient's ankle, where joints 20 and 20a thereby enable connected pivoting motion between shell 4 and shell 19.

With further reference to FIGS. 1-4, the orthosis boot also includes a locking plate assembly 10 that is fixedly connected to posterior shell 4 by a fastener 28 and is connected to foot shell 19 by a pin 14, where plate 10 includes a slot 11 within which pin 14 is disposed. Plate 10 is able to move relative to pin 14 with pin 14 traveling within slot 11 as plate 10 moves relative to foot shell 19 when posterior shell 4 and foot shell 19 move or are adjusted relative to one another. Slot 11 further includes a locking slot portion 11a within which pin 14 may be positioned to fix the orientation of orthosis and inhibit movement of posterior shell 4 and foot shell 19 relative to one another.

Figure 1:
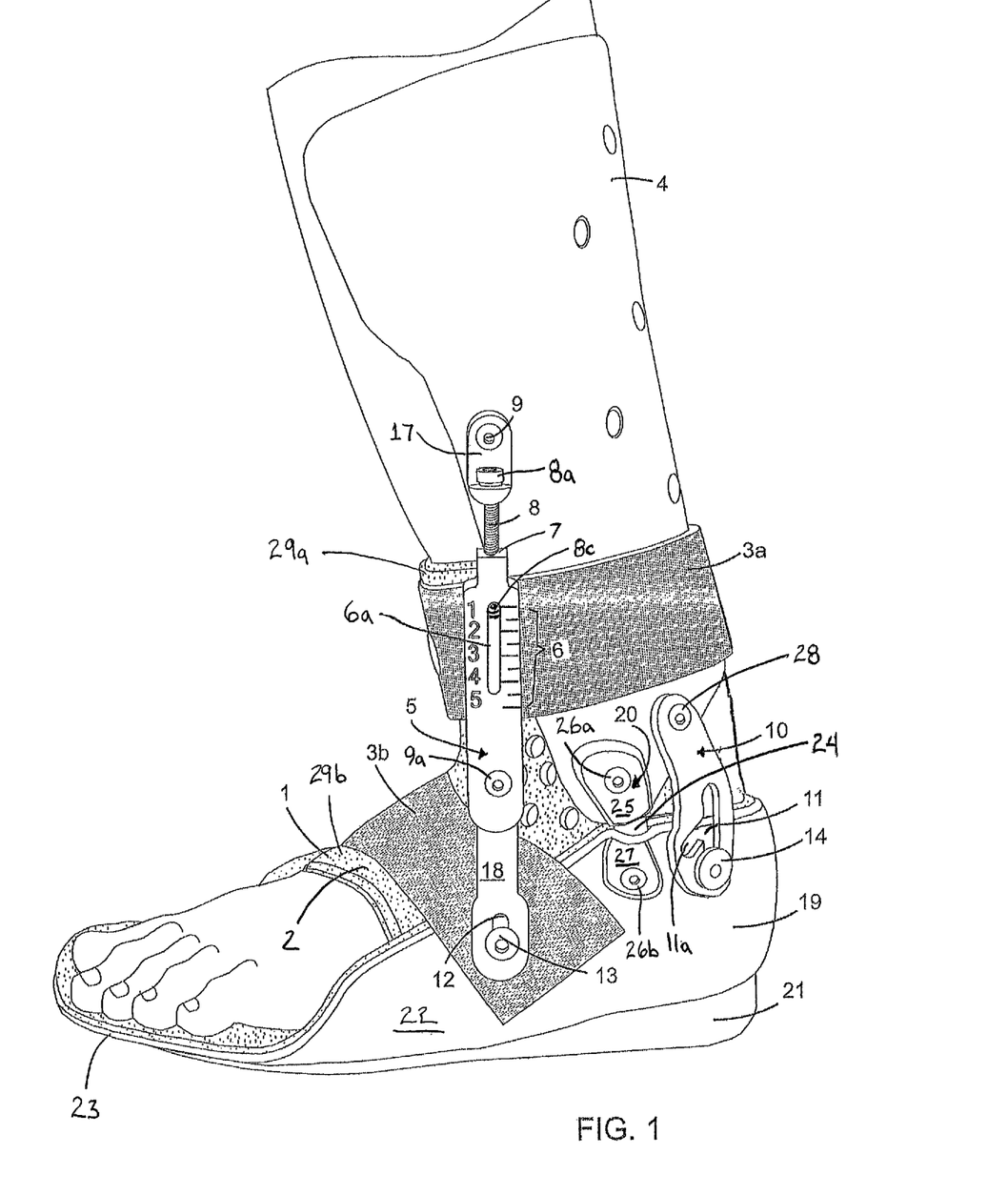
FIG. 1 is a perspective assembled view of an orthosis boot in accordance with the present invention illustrating a patient's foot and lower leg inserted therein and shown in a dorsiflexion position.
Figure 2:
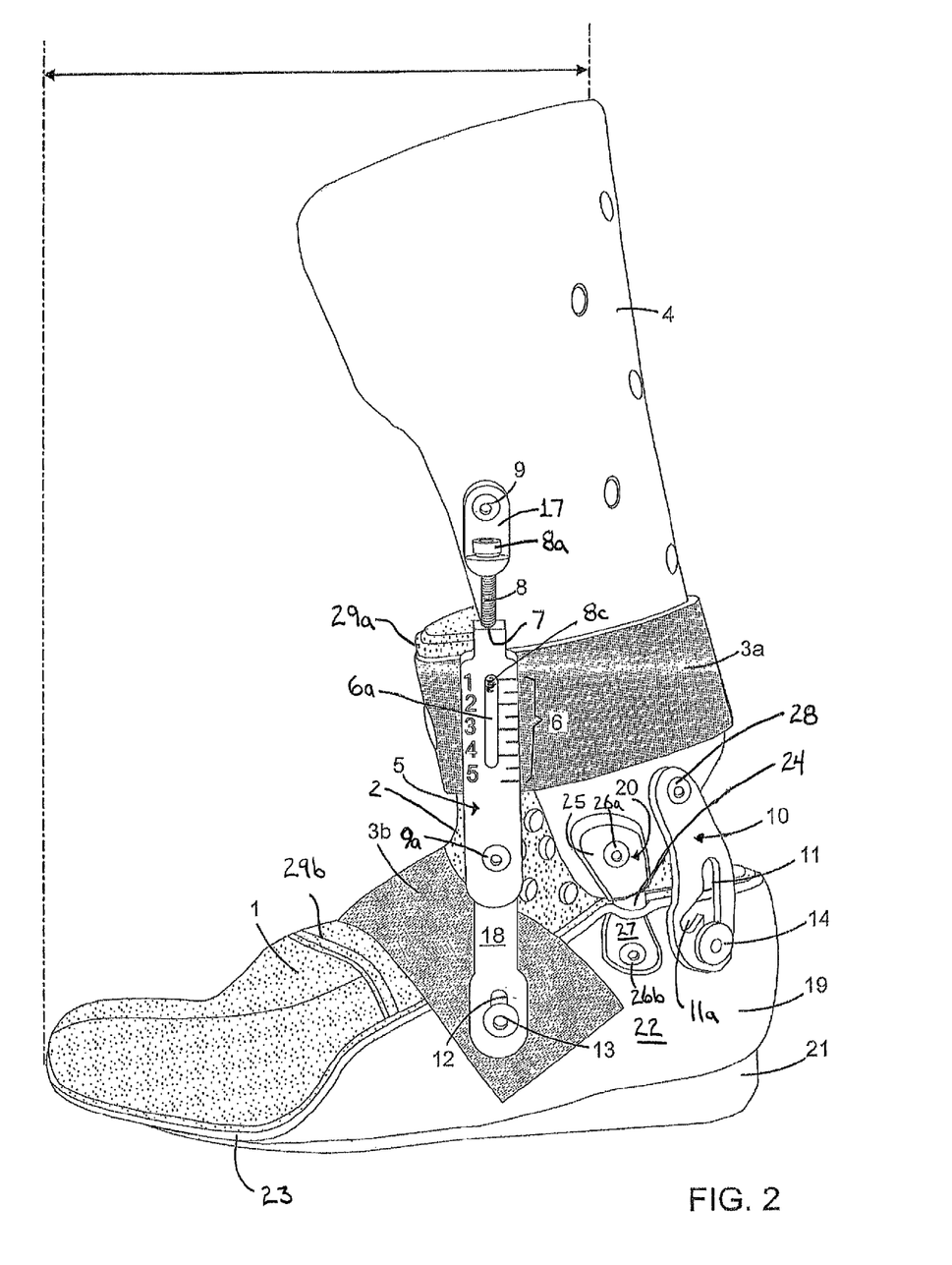
FIG. 2 is a perspective view of the orthosis of FIG. 1 with the patient's foot and leg removed disclosing the molded inner boot assembly.
Figure 3:
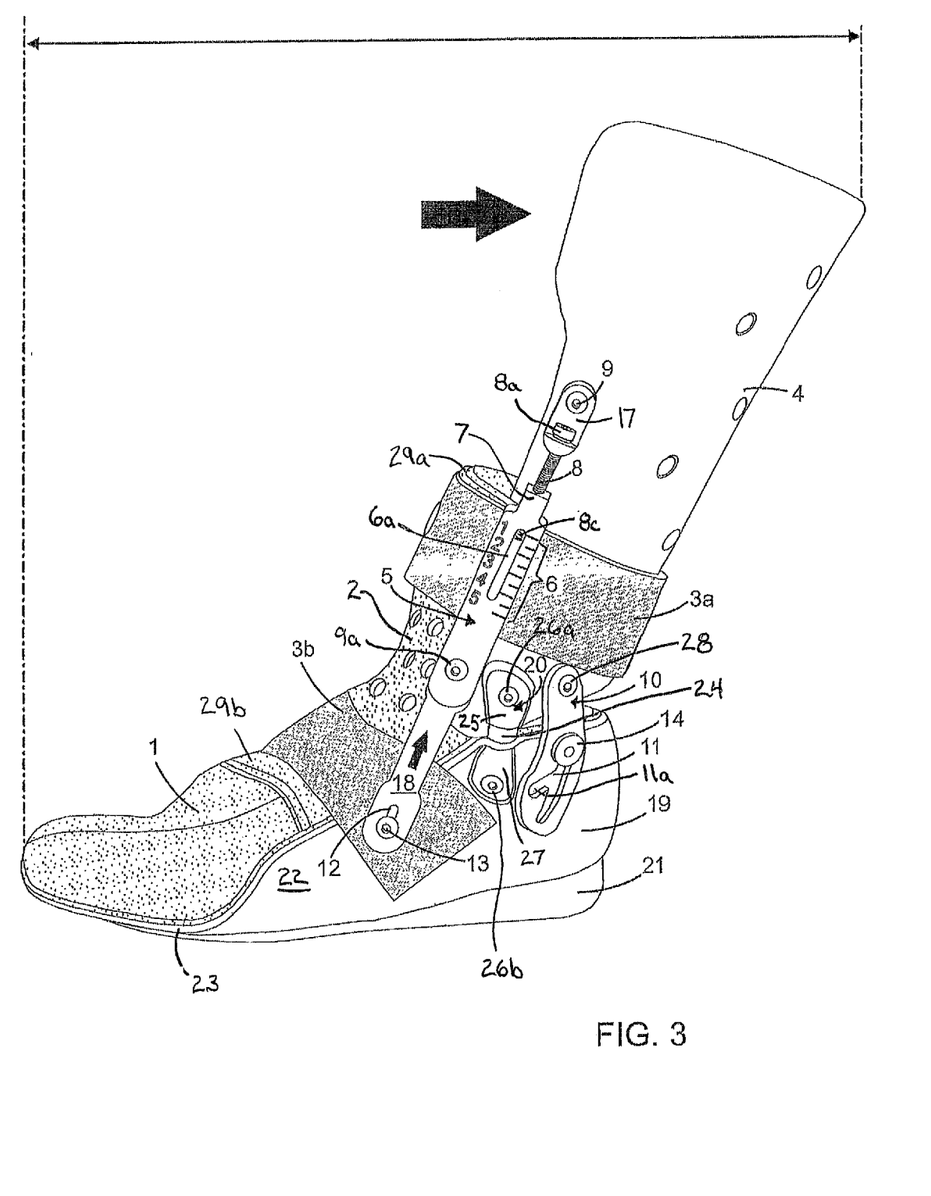
FIG. 3 is a perspective view of the orthosis of FIG. 2 in the plantar flexion position.
Figure 4:
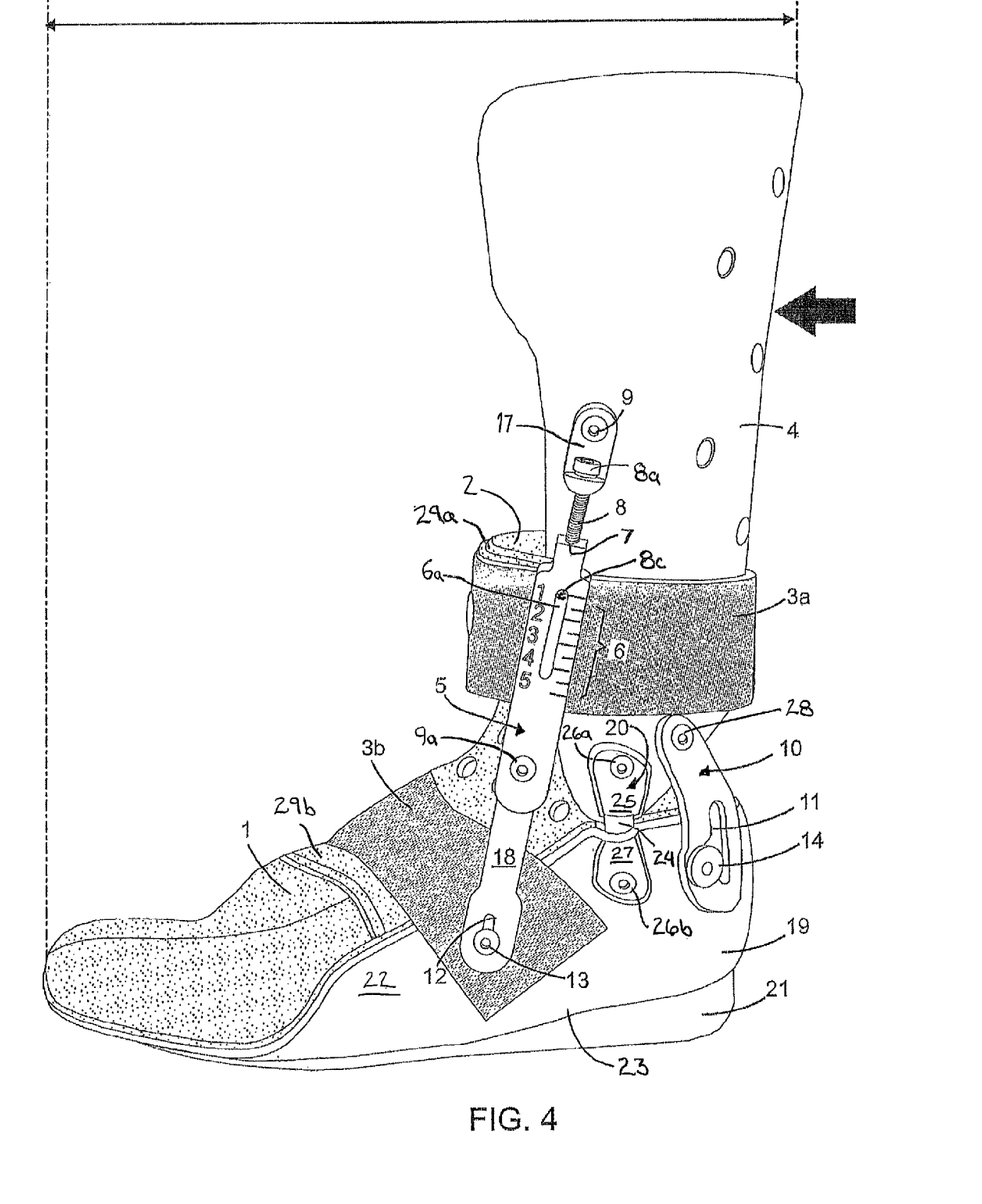
FIG. 4 is a perspective view of the orthosis of FIG. 2 in a locked position.

FIGS. 1 and 2 illustrate the orthosis in a dorsiflexion position in which pin 14 is slid downward to be positioned toward at the bottom portion of an end of slot 11. In this orientation shell 19 is unable to further pivot upwardly relative to shell 4 even under tension from assembly 5 due to the engagement of pin 14 with the bottom closed end of slot 11. FIG. 3 illustrates the orthosis in a plantar flexion position in which pin 14 is slid upward to be positioned toward at the top upper portion of slot 11 at the opposite end of slot 11 relative to FIGS. 1 and 2. As further understood from FIG. 3, when in the plantar flexion position the molded inner boot 1 and posterior shell 4 are tilted, as indicated by the arrow, with elastomer band 18 of assembly 5 being stretched and extended. FIG. 4 illustrates the orthosis in the locked orientation with pin 14 positioned within locking slot portion 11a. As understood from FIG. 4, the orthosis is placed in a generally 90 degree or right angle orientation when in the locked position, such as understood from the relative orientation of posterior shell 4 and foot shell 19, with the alignment of assembly 5 correspondingly being shown when the orthosis is in the locked position.

Figure 5:
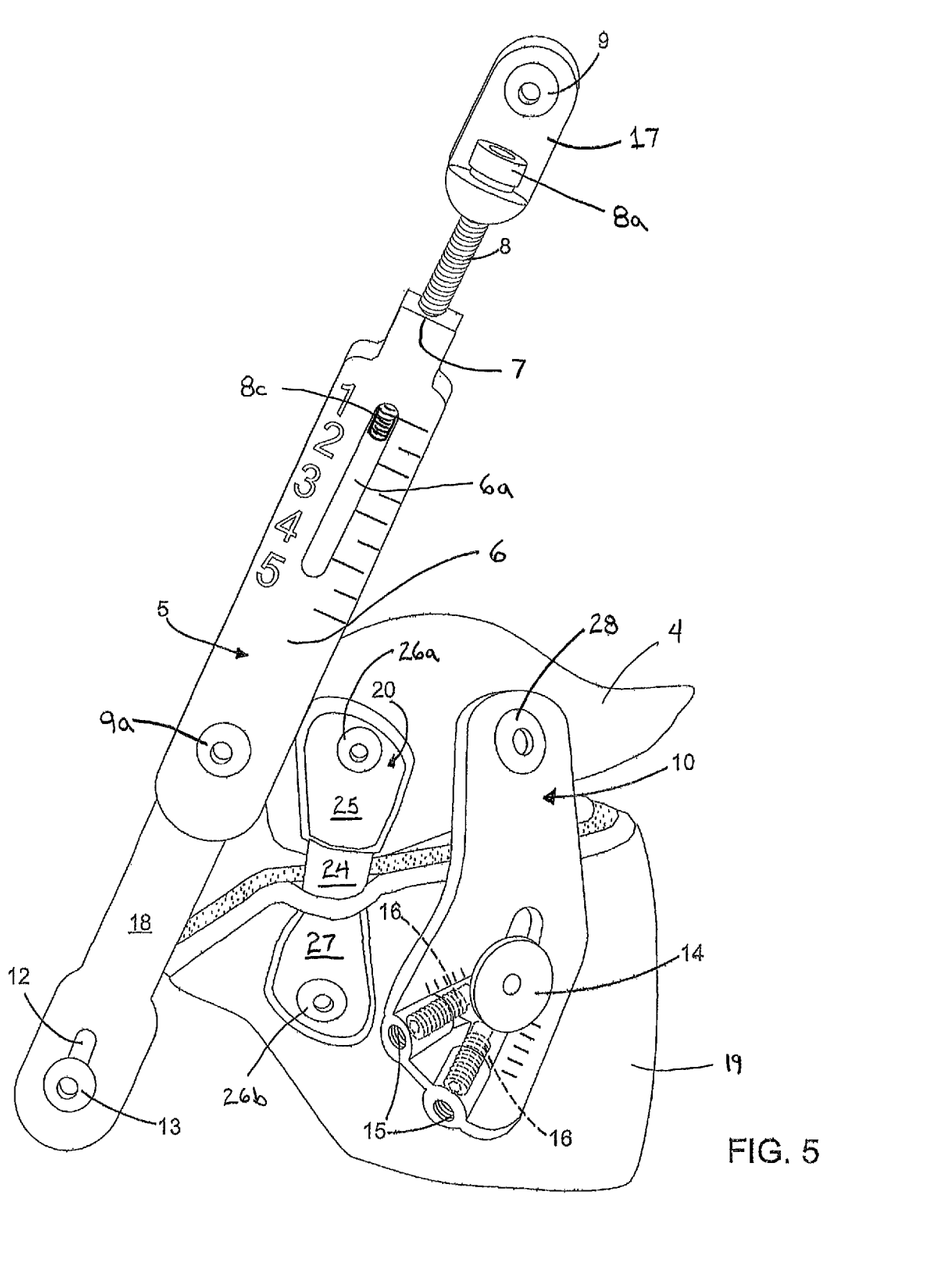
FIG. 5 is a partial perspective view of components of the orthosis in accordance with another aspect of the present invention illustrating the inter-relationship of an alternative adjustable slotted locking plate assembly with an adjustable tension assembly, and ankle joint for providing tension in the variable locking positions for ROM improvement.
Figures 6, 7:
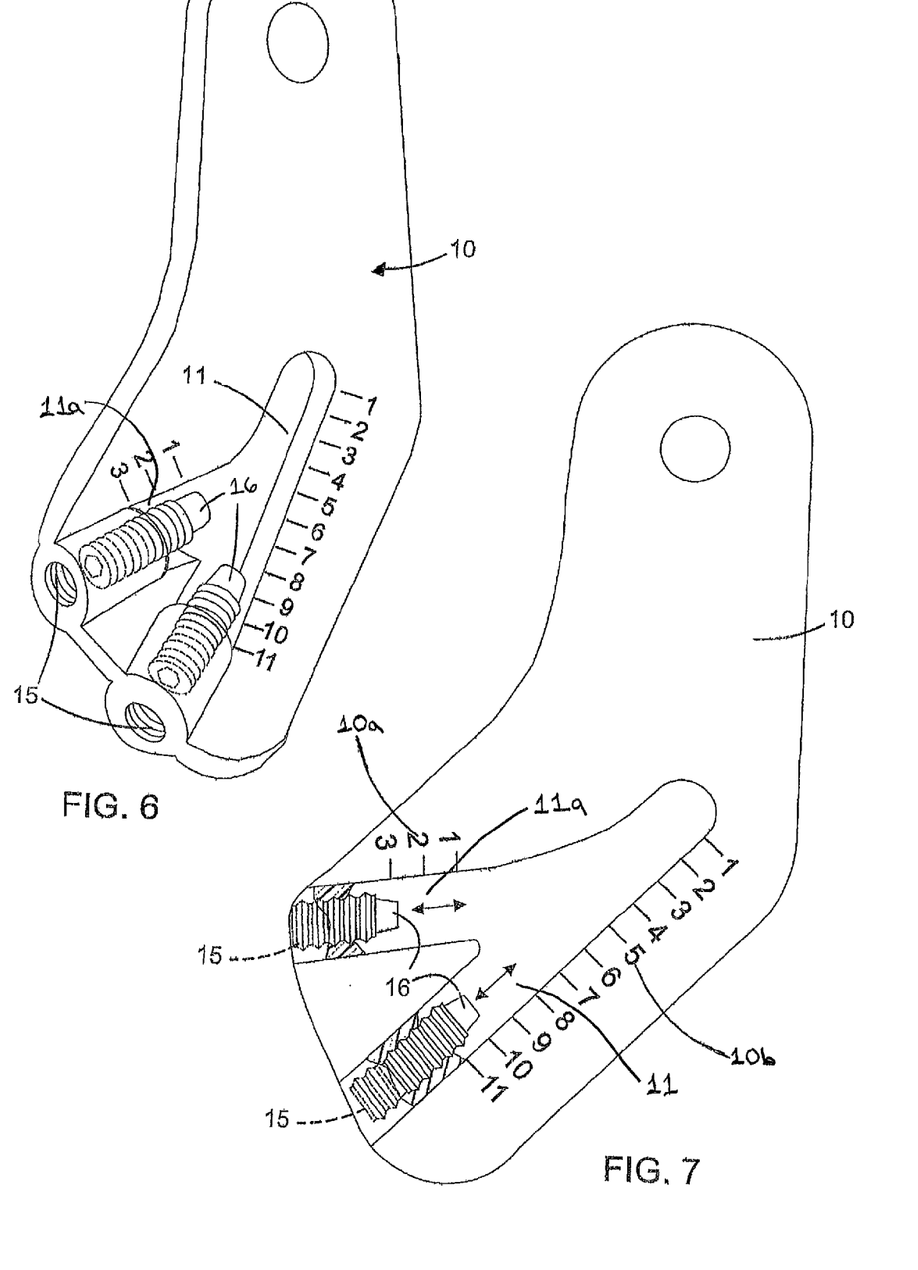
FIG. 6 is a perspective view of the plate assembly of FIG. 5 showing adjustable set screws for selectively setting parameters of the orthosis.
FIG. 7 is a partial cutaway view of the plate assembly of FIG. 5.

As best understood from FIGS. 5 to 7, and as discussed in pending U.S. application Ser. No. 12/658,427, plate 10 may further include a pair of threaded holes or bores 15, with one of bores 15 being aligned with slot 11 and the other with locking slot portion 11a. Bores 15 receive threaded adjustment screws 16 for adjusting the amount of travel of pin 14 within slot 11 and locking slot portion 11a. As shown in FIG. 7, numerical gradation or indicia 10a, 10b are provided adjacent locking slot portion 11a and slot 11, respectively, that provide a visual indicator for setting and monitoring the adjustment of screws 16. For example, by adjusting the screw 16 aligned with slot 11 to extend further into slot 11, the amount pin 14 can travel within slot 11 is thereby decreased, which thus limits the amount of flex obtained in the dorsiflexion position—that is, the amount the foot of a patient is able to be flexed upward by the orthosis is decreased. The point at which pin 14 contacts the lower portion of slot 11 or the screw 16 associated with slot 11 may be referred to as a variable locked position as the lower shell 19 will no longer pivot upward relative to upper shell 4 even under the force of tension assembly 5.

As discussed in more detail below, the tension assembly 5 and adjustable locking plate assembly 10 work in conjunction with the ankle joints 20, 20a that connect the upper posterior shell 4 to the foot shell 19 during use of the orthosis.

Figure 8:
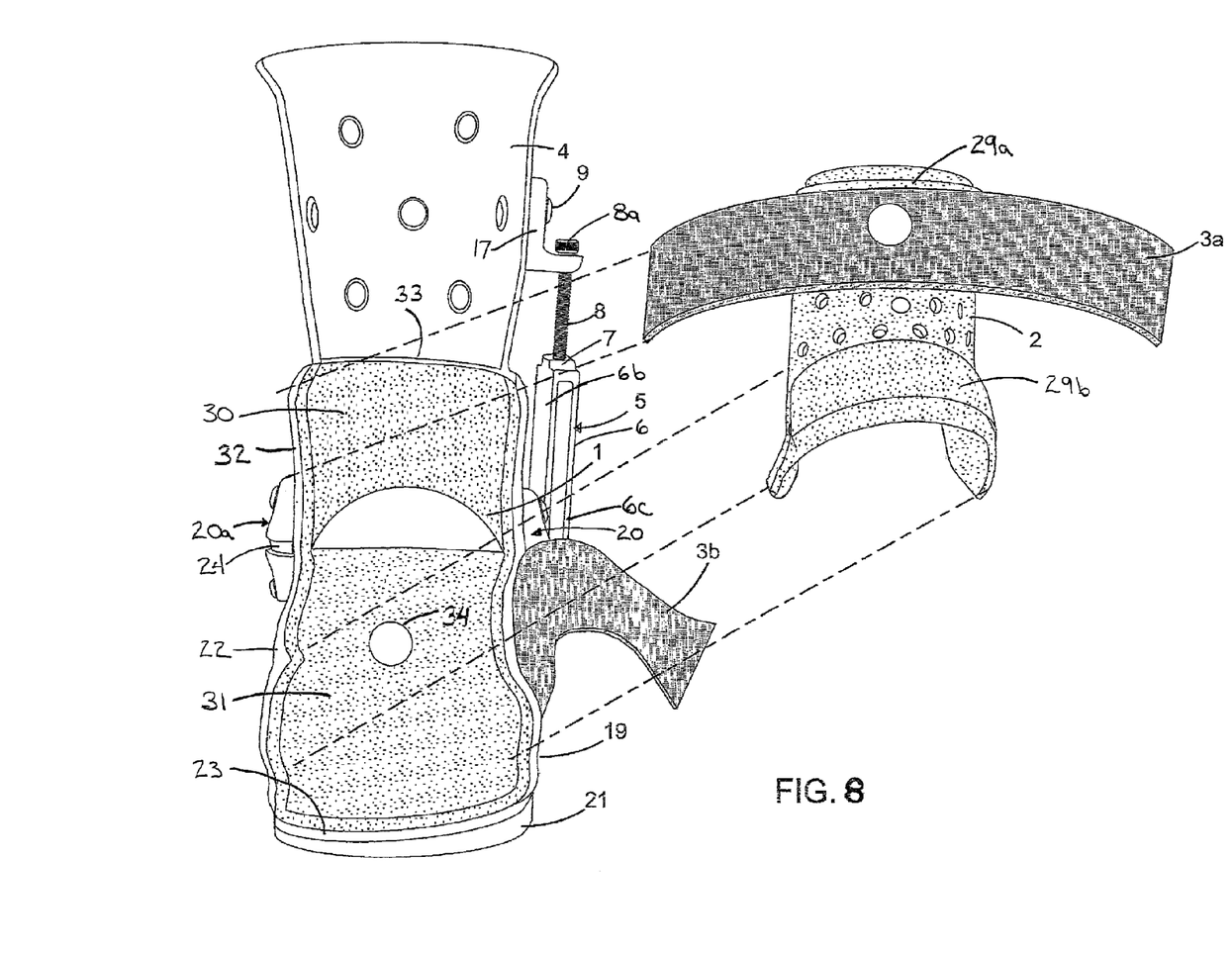
FIG. 8. is an exploded assembly view of the orthosis of FIG. 2 disclosing the tongue removed from the molded inner boot assembly.
Figure 9:
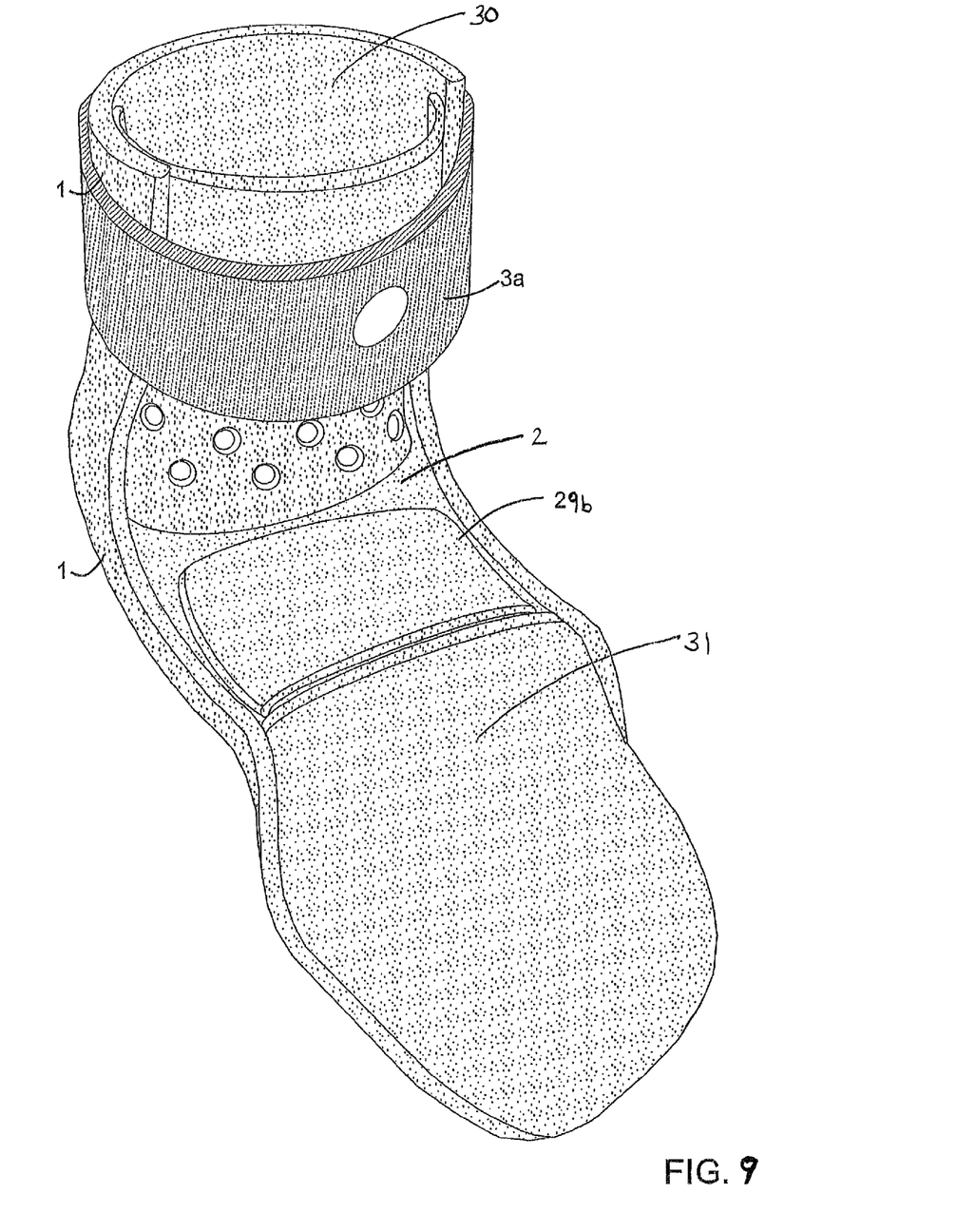
FIG. 9 is a perspective view of the molded inner boot assembly including the posterior section and the anterior section with the tongue of the inner boot and straps

Referring now to FIGS. 8 and 9, the molded inner boot assembly 1 is constructed to be relatively compliant to form a padding and may be made, for example, of polyethylene or ethylene vinyl acetate (EVA), or the like. Molded inner boot assembly 1 includes a removable tongue 2 to which is affixed elastic strap 3a that is used to fasten tongue 2 to posterior shell 4, where tongue 2 is formed to be positioned over the anterior foot and ankle area of a patient when the patient's foot is placed within the orthosis and strap 3a is secured to the rear of posterior shell 4 by a hook and loop fastener. The stretchable elastic strap 3a allows for tibial rotation during dorsi and planter flexion. Tongue 2 includes air holes, as well as an upper pad 29a and a lower pad 29b forming thicker portions whereat straps 3a and 3b engage with tongue 2.

Molded inner boot assembly 1 further includes an upper or posterior lining section or portion 30 and a lower or anterior lining section or portion 31, where upper lining section 30 is affixed to posterior shell 4 and lower lining section 31 is affixed to foot shell 19. Upper lining section 30 and lower lining section 31 may be molded together as a single piece, as shown in FIG. 9, and subsequently separated in to two separate pieces for installation in the respective shells 4 and 19. Posterior shell 4 includes a lower recess 32 within which upper lining section 30 is affixed to provide a smooth transition between the interior surface of posterior shell 4 and upper lining section 30 at location 33. Lining sections 30 and 31 may be affixed to posterior shell 4 and foot shell 19, respectively, by an adhesive.

As shown in FIG. 8, an aperture 34 is provided in the heel area of lower lining section 31 and foot shell 19 through which the orientation of a patient's heel within the orthosis may be visibly observed when fitting the orthosis to the patient to insure proper installation. FIG. 8 further discloses that tension adjuster 6 includes a pair of legs 6b, 6c, where elastomer band 18 is mounted between legs 6b, 6c.

In operation, a patient's foot is placed within the orthosis, such as when the orthosis is in the locked position of FIG. 4 where pin 14 is positioned within locking slot portion 11a. Tongue 2 is then placed over the patient's foot with verification that the patient's heel is properly located by viewing through aperture 34. Strap 3a is then secured over the patient's lower leg area by affixing strap 3a to the rear portion of posterior shell 4 and strap 3b is secured over the patient's upper foot portion by securing the end of strap 3b opposite pin 13 to the other side of shell 19. Upon removing the orthosis from the locked position by moving lower shell 19 to remove pin 14 from locking slot portion 11a, the adjustable tension assembly 5 may then be adjusted and used to apply an upward force to shell 19 relative to shell 4 for promoting dorsiflexion movement of the patient to prevent contracture, and to stretch and increase range of motion of the patient's heel cord.

Adjustable tension assembly 5 is employed to selectively adjust the amount of upward force that may be imparted to a patient. By tightening bolt 8, tension adjuster 6 is drawn upwards along the threaded shaft of bolt 8, where bolt 8 is held stationary via the retention of head 8a in bracket 17. This in turn causes elastomer band 8 to be axially stretched, thereby increasing the upward force applied to lower shell 19 by tension assembly 5 for a given position of shell 19 relative to shell 4. The level of tension applied may be set and monitored via the gradations provided on tension adjuster 6, with a lower end 8c of bolt 8 being visible through the aperture 6a in tension adjuster 6 that is aligned with the gradations. Accordingly, the amount of tension applied to a patient to promote stretching of their heel cord may be progressively increased over time.

Still further the plate assembly 10 of FIGS. 5 and 6 may be used in conjunction with the selective adjusting of tension assembly 5 to monitor and progressively stretch a patient's heel cord. It should be appreciated that as a patient's heel cord is stretched pin 14 will travel downward along slot 11 starting at a maximum plantar flexion position as illustrated in FIG. 3 where pin 14 is located fully upwards within slot 11, or in some orientation of pin 14 along slot 11 other than in the position of FIGS. 1 and 2. The amount of stretch may be observed and monitored by the position of pin 14 relative to the indicia provided adjacent slot 11. To limit the amount of tension applied to a patient, or the amount of tension applied over a given range of movement of shell 19 relative to shell 4, the screw 16 within the bore 15 associated with slot 11 may be adjusted to project further into slot 11. When screw 16 is extended into slot 11, pin 14 will come into contact with screw 16 and prevent further movement of shell 19 relative to shell 4. It is desirable to obtain a normal resting position of a patient's foot in a position such that pin 14 is seated within slot 11, such as against screw 16, without the patient applying a downward force against shell 19. Once obtained, screw 16 associated with slot 11 may be further retracted to allow further upward movement of shell 19 relative to shell 4, which adjustment to screw 16 of slot 11 may be performed in combination with an adjustment of assembly 5 to increase upward tension on shell 19. The adjustable features of the locking assembly 10, with its variable positions, enable a care giver to adjust in predetermined positions for optimum range of motion control in dorsi and plantar flexion.

The orthosis may be employed to apply dorsiflexion tension to a patient until the normal resting position of a patient's foot is in a position where pin 14 is seated against the lower base end of slot 11, such as shown in FIGS. 1 and 2, without the patient applying a downward force against shell 19. With reference to the embodiments of FIGS. 6 and 7, this position is obtained when the screw 16 associated with slot 11 is fully retracted such that it does not impede travel of pin 14 within slot 11. In the illustrated embodiment of FIGS. 1 and 2, the orthosis provides an approximate 18 to 22 degree upward orientation of shell 19 relative to shell 4 from perpendicular, such as relative to the orientation of FIG. 4. Monitoring of the obtained at rest orientation of a patient's foot within the orthosis may be done at night, for example, where spastic patients are in a relaxed state such that they are not applying a downward counter force to lower shell 19.

The screw 16 associated with locking slot portion 11*a* may be used to provide an increased plantar flexion orientation of shell 4 relative to shell 19, such as, for example, when fitting to patients to accommodate specific conditions of the patient.

Figure 10:
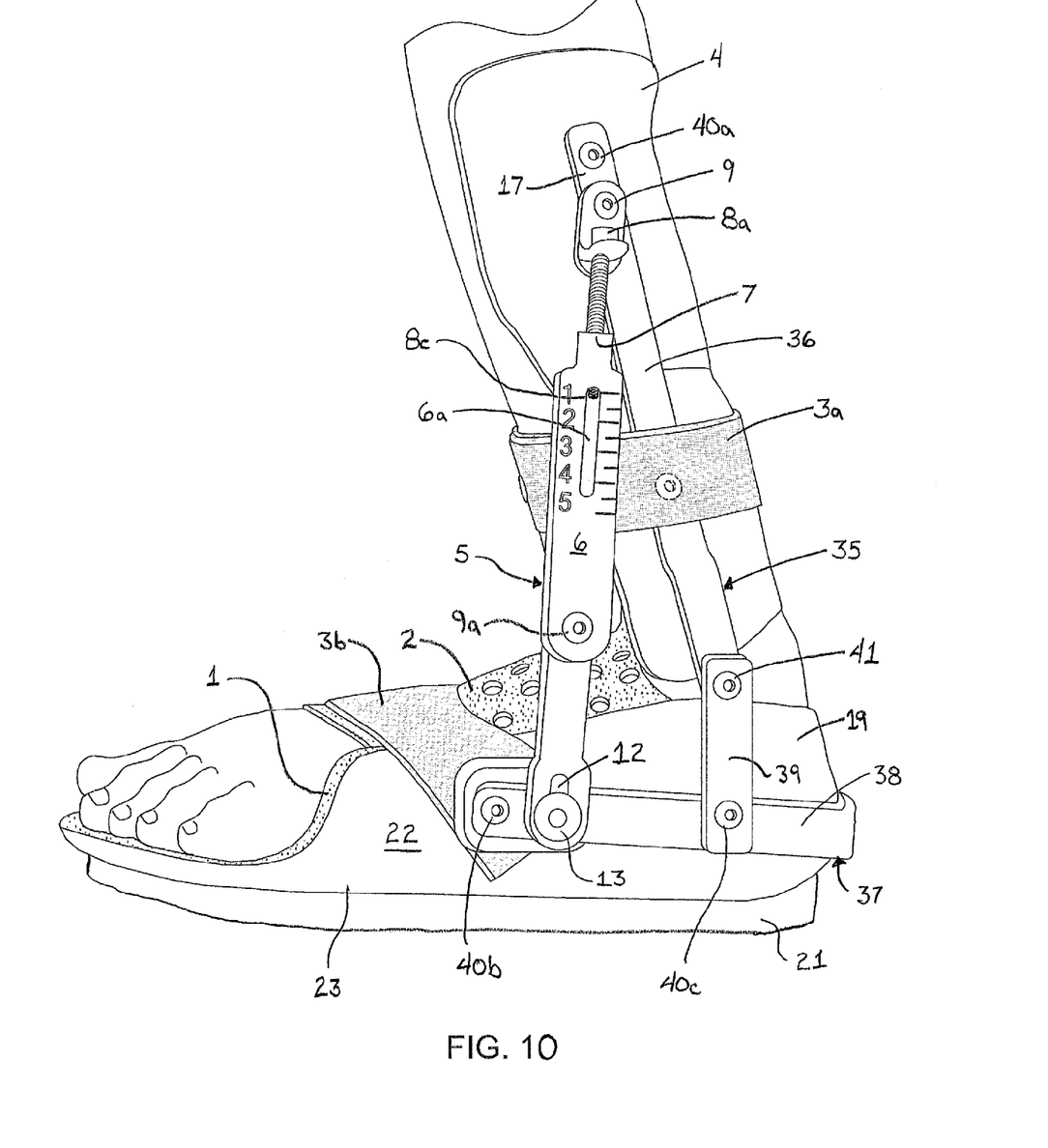
FIG. 10 is a perspective assembled view of an alternative orthosis boot in accordance with the present invention illustrating a patient's foot and lower leg inserted therein.
Figure 11:
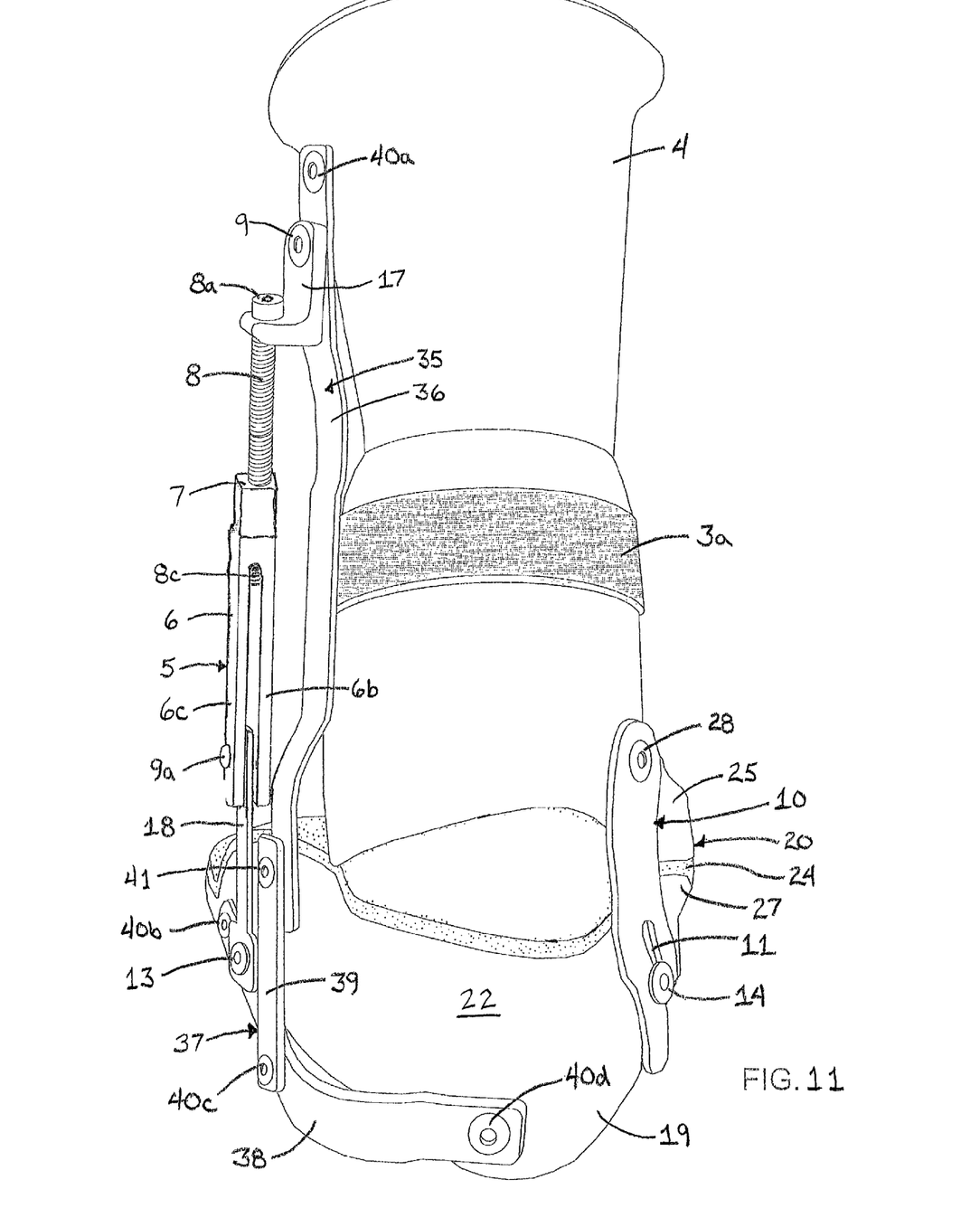
FIG. 11 is a rear perspective view of the orthosis boot of FIG. 10 with the patient's foot and leg removed.

Referring now to FIGS. 10 and 11, an alternative orthosis in accordance with the present invention is disclosed that includes a brace assembly 35 mounted to the upper shell 4 and lower shell 19, with a tension assembly 5 mounted to the upper shell 4 and lower shell 19 at brace assembly 35 whereby brace assembly 35 functions as an anchor for tension assembly 5. Brace assembly 35 provides support to the orthosis, and in particular with regard to higher force settings of tension assembly 5 that may be employed with larger patients, such as older or larger children, or adults. Moreover, brace assembly 35 provides additional restrictive motion to the orthosis and thereby direct the relative motion of upper shell 4 and lower shell 19 with respect to each other. Due to the similarities between the orthosis of FIGS. 10 and 11 relative to the orthosis of FIGS. 1-4, not all of the like referenced parts will be discussed herein.

Brace assembly 35 includes an upper brace 36 and a lower brace 37, with lower brace 37 forming a stirrup comprising a heal or base section 38 and a joint section 39, where upper brace 36, base section 38 and joint section 39 are constructed of a rigid material, such as aluminum in the illustrated embodiment. Upper brace 36 comprises an elongate member that is secured by fasteners to upper shell 4 to prevent relative movement thereto, including fastener 40*a* and an additional fastener that is covered by strap 3*a* in the views of FIGS. 10 and 11. Bracket 17 is mounted to upper brace 36 by fastener 40*a* to connect the upper end of tension assembly 5 to brace assembly 35.

Base section 38 comprises a generally J-shaped member that extends from behind the heal area of shell 19 along the wall portion 22 positioned adjacent the lateral side of a patient's foot, with base section 38 being affixed to lower shell 19 by fasteners, including fasteners 40*b*, 40*c* and 40*d*. As shown, fastener 40*b* is also used to retain strap 3*b* to lower shell 19 and fastener 40*c* is used to fixedly connect joint section 39 to base section 38 to prevent relative movement therebetween. Pin 13 is affixed to base section 38, with elastomer band 18 connected to pin 13 by way of slot 12 in band 18 to connect the opposite end of tension assembly 5 to brace assembly 35.

Upper brace 36 and joint section 39 are connected together for pivoting movement by a pivot pin 41 that allows upper shell 4 and lower shell 19 to move relative to each other during movement of a patient's foot. Although lower brace 37 is shown as comprising two separate components in the illustrated embodiment, that being base section 38 and joint section 39, it should be appreciated that an alternative lower brace 37 may be constructed as a unitary member.

As shown in FIG. 11, the orthosis further includes a plate assembly 10 located on the side opposite of tension assembly 5, where assembly 10 includes a slot 11 within which pin 14 is able to slide during relative movement of upper shell 4 and lower shell 19. Also included on the orthosis as shown in FIG. 11 is a flexible ankle joint 20, with ankle joint 20 being positioned adjacent plate assembly 10.

The present invention provides a lightweight orthosis to increase a patient's range of motion while providing proper foot alignment, along with comfort such as by way of the inner boot assembly, where the orthosis thus prevents muscle shortening and contracture of the heel cord and increasing the ROM. Changes and modifications in the specifically described embodiments, however, can be carried out without departing from the principles of the present invention which is intended to be limited only by the scope of the appended claims, as interpreted according to the principles of patent law including the doctrine of equivalents. For example, an additional second tension adjust assembly could be incorporated in the orthosis on the opposite side of the patient's foot to that shown in the embodiment of FIG. 1—that is, an additional tension adjust assembly may be provided on the medial or interior side of the orthosis in addition to tension assembly 5 shown on the lateral or exterior side. Still further, although strap 3*b* is shown as affixed to foot shell 19 on the lateral side and noted as including hook and loop connectors for fastening to the medial side of foot shell 19, it should be appreciated that an alternative static strap for retaining the orthosis on a patient's foot may be fixedly connected to the medial side and selectively secured to the lateral side, such as by a hook and loop fastener. Moreover, an orthosis may include a strap on each side, with the straps being secured by crossing the straps over one another for additional holding force.

What is claimed is:

1. An ankle foot orthosis comprising:
   an upper leg portion and a lower foot portion, said lower foot portion configured to receive a patient's foot with said upper leg portion configured to engage a posterior ankle portion of the patient when the patient's foot is received within said lower foot portion, said upper leg portion and said lower foot portion being connected together and moveable with respect to each other when worn by the patient;
   an adjustable tension assembly connected to said upper leg portion and said lower foot portion, said adjustable tension assembly operative to provide an upward biasing force to the patient's foot when received within said lower foot portion;
   said adjustable tension assembly including a first portion connected to a second portion, with said first portion including a straight threaded member having an elongate axis and said first portion including a tension adjuster having a bore for receiving said threaded member, and said second portion including an elastomer band having an elongate axis, with an end of said elastomer band being connected at a connection to said tension adjuster with said elongate axis of said elastomer band and said elongate axis of said threaded member being in coaxial alignment along the same axis, said tension adjuster being operable to move said end of said elastomer band connected to said tension adjuster to axially stretch said elastomer band along said elongate axis of said elastomer band to selectively increase or decrease an amount of axial stretch applied to said elastomer band to provide a selectable upward biasing force, wherein said tension adjuster includes indicia for observing said amount of axial stretch applied to said elastomer band.

2. The ankle foot orthosis of claim 1 further including a plate assembly connected with said upper leg portion and said lower foot portion, said plate assembly including a slot with said ankle foot orthosis further including a pin, said pin being configured to move within said slot when said upper leg portion and said lower foot portion are moved relative to each other.

3. The ankle foot orthosis of claim 2, wherein said plate assembly further includes a locking slot portion extending from said slot, and wherein said pin may be positioned within said locking slot portion to orient said upper leg portion relative to said lower foot portion at an approximate right angle.

4. The ankle foot orthosis of claim 3, wherein said plate assembly further includes an adjustment screw aligned with said locking slot portion, and wherein said adjustment screw is configured to be adjustably projected into said locking slot portion.

5. The ankle foot orthosis of claim 2, wherein said plate assembly is fixedly connected to said upper leg portion and said pin is affixed to said lower foot portion.

6. The ankle foot orthosis of claim 2, wherein said plate assembly further includes an adjustment screw aligned with said slot, and wherein said adjustment screw is configured to be adjustably projected into said slot to limit an amount said upper leg portion and said lower foot portion are able to move with respect to each other in a dorsiflexion orientation.

7. The ankle foot orthosis of claim 2, wherein said plate assembly includes indicia adjacent said slot for observing a position of said pin within said slot.

8. The ankle foot orthosis of claim 1, wherein said upper leg portion comprises an upper shell and said lower foot portion comprises a lower shell defining a heel receiving cavity, and wherein said ankle foot orthosis further includes an inner boot assembly joined to interior regions of said upper shell and said lower shell.

9. The ankle foot orthosis of claim 8 further including a strap, said strap being removably connectable to one of said upper shell or said lower shell over the patient's foot or ankle to retain said ankle foot orthosis on the patient.

10. The ankle foot orthosis of claim 9, wherein said inner boot assembly includes a tongue, and wherein said tongue is held in place over the patient by said strap.

11. The ankle foot orthosis of claim 8, wherein said upper shell includes a cavity and wherein said inner boot assembly includes an upper portion, said upper portion being received within said cavity.

12. The ankle foot orthosis of claim 1, wherein said threaded member is fixed relative to said upper leg portion at an opposite end from where said threaded member engages said tension adjuster, with said threaded member being rotatable to increase or decrease said amount of axial stretch applied to said elastomer band.

13. The ankle foot orthosis of claim 12 further including a bracket fixed to said upper leg portion with said threaded member including a head and with said head being received within said bracket.

14. The ankle foot orthosis of claim 1 further including a brace assembly, said brace assembly including an upper brace fixedly connected to said upper leg portion and a lower brace fixedly connected to said lower foot portion, wherein said upper brace and said lower brace comprise rigid members that are joined together for pivoting movement.

15. The ankle foot orthosis of claim 14 wherein said adjustable tension assembly is connected to said upper brace and said lower brace.

16. The ankle foot orthosis of claim 1, wherein said elastomer band is connected to said lower foot portion at an end opposite from the connection of said elastomer band with said tension adjuster.

17. The ankle foot orthosis of claim 1 further including a pair of flexible joints, said flexible joints connecting said upper leg portion and said lower foot portion.

18. An ankle foot orthosis comprising:
an upper leg portion and a lower foot portion, said lower foot portion configured to receive a patient's foot with said upper leg portion configured to engage a posterior ankle portion of the patient when the patient's foot is received within said lower foot portion, said upper leg portion and said lower foot portion being connected together and moveable with respect to each other when worn by the patient;
an adjustable tension assembly connected to said upper leg portion and said lower foot portion, said adjustable tension assembly operative to provide an upward biasing force to the patient's foot when received within said lower foot portion;
said adjustable tension assembly including a first portion connected to a second portion, with said first portion including a straight threaded member having an elongate axis and said first portion including a tension adjuster having a bore for receiving said threaded member, and said second portion including an elastomer band having an elongate axis, with an end of said elastomer band being connected at a connection to said tension adjuster with said elongate axis of said elastomer band and said elongate axis of said threaded member being in coaxial alignment along the same axis, said tension adjuster being operable to move said end of said elastomer band connected to said tension adjuster to axially stretch said elastomer band along said elongate axis of said elastomer band to selectively increase or decrease an amount of axial stretch applied to said elastomer band to provide a selectable upward biasing force;
further including a plate assembly connected with said upper leg portion and said lower foot portion, said plate assembly including a slot with said ankle foot orthosis further including a pin, said pin being configured to move within said slot when said upper leg portion and said lower foot portion are moved relative to each other;
wherein said plate assembly further includes an adjustment screw aligned with said slot, and wherein said adjustment screw is configured to be adjustably projected into said slot to limit an amount said upper leg portion and said lower foot portion are able to move with respect to each other in a dorsiflexion orientation.

19. The ankle foot orthosis of claim 18, wherein said threaded member is fixed relative to said upper leg portion at an opposite end from where said threaded member engages said tension adjuster, with said threaded member being rotatable to increase or decrease said amount of axial stretch applied to said elastomer band.

20. The ankle foot orthosis of claim 19 further including a bracket fixed to said upper leg portion with said threaded member including a head and with said head being received within said bracket.

21. The ankle foot orthosis of claim 18, wherein said plate assembly further includes a locking slot portion extending from said slot, and wherein said pin may be positioned within said locking slot portion to orient said upper leg portion relative to said lower foot portion at an approximate right angle.

22. The ankle foot orthosis of claim 21, wherein said plate assembly further includes an additional adjustment screw aligned with said locking slot portion, and wherein said additional adjustment screw is configured to be adjustably projected into said locking slot portion.

23. The ankle foot orthosis of claim 18, wherein said elastomer band is connected to said lower foot portion at an end opposite from the connection of said elastomer band with said tension adjuster.

24. The ankle foot orthosis of claim 18, wherein said plate assembly is fixedly connected to said upper leg portion and said pin is affixed to said lower foot portion.

25. The ankle foot orthosis of claim 18, wherein said upper leg portion comprises an upper shell and said lower foot portion comprises a lower shell defining a heel receiving cavity, and wherein said ankle foot orthosis further includes an inner boot assembly joined to interior regions of said upper shell and said lower shell.

26. An ankle foot orthosis comprising:
   an upper leg portion and a lower foot portion, said lower foot portion configured to receive a patient's foot with said upper leg portion configured to engage a posterior ankle portion of the patient when the patient's foot is received within said lower foot portion;
   an adjustable tension assembly connected to said upper leg portion and said lower foot portion, said adjustable tension assembly operative to provide an upward biasing force to the patient's foot when received within said lower foot portion;
   said adjustable tension assembly including a first portion connected to a second portion, with said first portion including a tension adjuster and said second portion including an elastomer band, with said elastomer band being connected to said tension adjuster and said tension adjuster being operable to selectively increase or decrease an amount of axial stretch applied to said elastomer band to provide a selectable upward biasing force, and wherein said tension adjuster includes indicia for observing said amount of axial stretch applied to said elastomer band.

27. The ankle foot orthosis of claim 26 further including a plate assembly connected with said upper leg portion and said lower foot portion, said plate assembly including a slot with said ankle foot orthosis further including a pin, said pin being configured to move within said slot upon movement of said upper leg portion relative to said lower foot portion.

28. The ankle foot orthosis of claim 27, wherein said plate assembly is fixedly connected to said upper leg portion and said pin is affixed to said lower foot portion.

\* \* \* \* \*